(12) United States Patent
Song et al.

(10) Patent No.: US 12,405,196 B1
(45) Date of Patent: Sep. 2, 2025

(54) MEDICAL CATHETER TESTING DEVICE AND A TESTING METHOD THEREOF

(71) Applicant: Ningbo Linstant Polymer Materials Co., Ltd., Ningbo (CN)

(72) Inventors: Xiaobo Song, Ningbo (CN); Xiaopeng Li, Ningbo (CN)

(*) Notice: Subject to any disclaimer, the term of this patent is extended or adjusted under 35 U.S.C. 154(b) by 0 days.

(21) Appl. No.: 19/181,290

(22) Filed: Apr. 16, 2025

(30) Foreign Application Priority Data

Oct. 31, 2024 (CN) .......................... 202411538190.2

(51) Int. Cl.
| | |
|---|---|
| G01N 3/20 | (2006.01) |
| A61M 25/01 | (2006.01) |
| G01N 3/02 | (2006.01) |
| G01N 3/04 | (2006.01) |
| G01N 3/06 | (2006.01) |
| G01N 3/08 | (2006.01) |
| G01N 3/32 | (2006.01) |

(52) U.S. Cl.
CPC ........... *G01N 3/20* (2013.01); *A61M 25/0147* (2013.01); *G01N 3/08* (2013.01); *A61M 2209/02* (2013.01); *G01N 3/02* (2013.01); *G01N 3/04* (2013.01); *G01N 3/068* (2013.01); *G01N 3/32* (2013.01); *G01N 2203/0005* (2013.01); *G01N 2203/0017* (2013.01); *G01N 2203/0023* (2013.01); *G01N 2203/04* (2013.01); *G01N 2203/0641* (2013.01)

(58) Field of Classification Search
CPC ... G01N 2203/0005; G01N 2203/0017; G01N 2203/0023; G01N 2203/04; G01N 2203/0641; G01N 3/02; G01N 3/04; G01N 3/068; G01N 3/32; G01N 3/20; A61M 25/0147; A61M 2209/02
See application file for complete search history.

(56) References Cited

FOREIGN PATENT DOCUMENTS

| | | | | |
|---|---|---|---|---|
| CN | 117030492 A | * | 11/2023 | ............... G01N 3/20 |
| CN | 118500878 A | * | 8/2024 | ............... G01N 3/20 |

OTHER PUBLICATIONS

CNIPA Office action; Application No. CN202411538190.2 dated Dec. 12, 2024, original Chinese, pp. 1-3.
CNIPA Office action; Application No. CN202411538190.2 dated Dec. 12, 2024, English machine translation generated Apr. 16, 2025, pp. 1-3.

* cited by examiner

*Primary Examiner* — Jonathan M Dunlap
(74) *Attorney, Agent, or Firm* — Addison D. Ault; IPGentleman Intellectual Property Services, LLC (57) ABSTRACT

The present invention discloses a medical adjustable bend pipe testing device and a testing method thereof, comprising: a machine platform, a catheter clamping assembly linearly arranged on the machine platform, a first visual detection assembly parallelly arranged on one side of the catheter clamping assembly, a wire pulling force detection assembly arranged on the wire pulling end of the catheter, a bending force detection assembly arranged on one side of the bending adjustment section of the catheter and a second visual detection assembly located at the end of the catheter. A PLC controller and a data acquisition and analysis module for receiving test results and providing control signals are also provided on the machine platform. The PLC controller is connected with a control panel and a display panel to perform fatigue test on the catheter.

9 Claims, 7 Drawing Sheets

MEDICAL CATHETER TESTING DEVICE AND A TESTING METHOD THEREOF

CROSS-REFERENCE TO RELATED APPLICATION

This application claims priority to Chinese Patent Application No. 202411538190.2, filed on Oct. 31, 2024 before the China National Intellectual Property Administration, the disclosure of which is incorporated herein by reference in entirety.

TECHNICAL FIELD

The present invention relates to the technical field of medical product testing equipment, and specifically to a medical catheter testing device and a testing method thereof.

BACKGROUND

At present, physical performance testing is essential to ensuring that medical adjustable curved catheters can be used safely and effectively in clinical environments. It involves multiple specific test items to comprehensively evaluate the mechanical properties and durability of the catheter.

Among them, the fatigue resistance test simulates the fatigue of the catheter in actual application through repeated bending or stretching cycles to evaluate its durability and life under long-term use. Catheter testing devices in the prior art are only achievable via the pulling of the internal traction wire, which requires too much manual participation, introducing operator errors, and difficulties with automation.

SUMMARY

In view of the shortcomings of the prior art, the purpose of the present invention is to provide a medical catheter testing device. The above technical objectives of the present invention are achieved through the following technical solutions: A medical adjustable bend pipe testing device, comprising: a machine, a catheter clamping assembly linearly arranged on the machine, a first visual detection assembly arranged in parallel on one side of the catheter clamping assembly, a wire tension detection assembly arranged at the wire end of the catheter, and a bending force detection assembly arranged on one side of the bending section of the catheter and a second visual detection assembly located at the end of the catheter. The machine is also provided with a PLC controller and a data acquisition and analysis module for receiving test results and providing control signals, and the PLC controller is connected to a control panel and a display panel;

The catheter clamping assembly includes at least two clamping units arranged along the straight section axis direction of the catheter, and the clamping unit positions the catheter on the machine in a linearly stretched posture;

The wire tension detection assembly includes two tension units arranged at the wire end of the catheter, a tension meter and a wire drawing assembly connected to the tension units in sequence; The first visual detection component is movably arranged in a direction parallel to the straight section axis of the catheter, and monitors and records the surface features of the catheter during the test;

The bending force detection component is arranged on one side of the bending section of the catheter, and docks with the bending section after bending to obtain the bending force of the bending section under the current wire pulling stroke or tension value; The second visual detection component is arranged axially at the end facing the catheter, and monitors and feedbacks the horizontal position of the bending section of the catheter, and the bending force detection component is arranged facing the second visual detection component to obtain the reading of the bending force of the bending section;

The control panel is electrically connected to the wire pulling force detection component, and controls and feedbacks the current tension value and wire pulling stroke of the tension unit;

The display panel is electrically connected to the first visual detection component and the second visual detection component, and obtains, displays and records the bending angle, bending radius and bending force under the current tension value and wire pulling stroke, as well as the current posture of the bending section. Further, the second visual detection component and the bending force detection component define a bending force detection area at the end of the catheter, the wire tension detection component defines a tension detection area at the front end of the catheter, and the first visual detection component is arranged above the machine and moves linearly between the tension detection area and the bending force detection area.

Further, the bending force detection area is provided with a shading plate close to the boundary of the bending force detection area, and the shading plate is provided with a through hole for the catheter to pass through.

Further, the machine is provided with a mounting slot, wherein the wire tension detection component is placed in the mounting slot, the tension unit extends out of the mounting slot, and the tension unit has a clamping plane for fixing the wire, and the clamping plane is flush with the straight section axis of the catheter.

Further, the bending force detection component includes a universal bracket, a metering dial movably arranged on the universal bracket, and a force measuring probe extending from the metering dial, the force measuring probe is arranged on one side of the straight section axis direction of the catheter, and receives the bending section of the bent catheter to detect the bending force of the bending section of the catheter.

Furthermore, the control panel also displays the current actuation position of the tension unit, the number of stretches in the current test phase, the preset test tension, the real-time tension, stretching speed and stretching number in the test phase through the PLC controller;

The control panel also displays the moving speed and current position of the first visual detection component through the PLC controller.

Furthermore, the display panel obtains the current posture of the catheter through the first visual detection component, and obtains the current reading and posture of the bending force detection component through the second visual detection component, and the second visual detection component obtains the reference position according to the straight section axis of the catheter, and defines a horizontal detection area on both sides of the reference position, and the second visual detection component obtains the bending section in the horizontal detection area to calculate the horizontal angle of the bending section.

The present invention also provides a test method for a medical adjustable bend pipe test device, comprising the following steps:

S1, mounting the catheter on the machine platform, and fixing the catheter through a clamping unit after adjusting the horizontality of the catheter, and then connecting the bending adjustment wire to the tension unit;

S2, setting the tension test parameters, and setting the number of cycles in the current test phase;

S3, the wire tension test component is activated, and the two tension units reciprocate to pull the wire;

S4, the bending force detection component tests the bending force, and the first visual detection component collects the image of the bending section of the catheter after bending in place, and fits and records the bending radius and bending angle, and records the tension value during the cyclic bending process;

S5, outputting a report. Further, the second visual detection component is a 3D scanning imaging system, and the second visual detection component obtains the geometric information of the bending section of the catheter and establishes a three-dimensional model.

Furthermore, the PLC controller, display panel and control panel are also connected to a computer processing system, which includes at least a data acquisition and analysis module and performs the following steps:

In step S1, the test phase and quality control rule conditions are planned, and a storage database is constructed according to the test phase. The test phase refers to setting the expected working posture of the bending section and testing the tension test data under the current posture, or setting the expected tension value, testing the working posture and wire position of the bending section, or setting the predetermined wire position, testing the working posture and tension value of the bending section;

In step S2, the current horizontal position of the catheter is retrieved. If the catheter is within the predetermined horizontal detection area, the current horizontality data of the catheter is retrieved and matched to the horizontal detection range. If the horizontality data does not meet the horizontal detection range, an error is reported on the control panel or display panel, and the PLC controller controls the pull wire tension detection component to return to its position; if the horizontality data is within the horizontal detection range, the PLC controller drives the pull wire tension detection component to act;

In steps S3 and S4, the test data and the surface features of the catheter, as well as the number of actions, are acquired and collected. The test data includes tension test data and bending section geometry information, as well as three-dimensional data of the bending posture of the bending section, and the items and values of the test data are mapped to the storage database;

In step S5, the test data is matched with the expected quality control rule conditions, and the test stage data groups that pass and fail the quality control are marked respectively, and the data report is output.

Compared with the prior art, the present invention has the following advantages and beneficial effects:

1. The bending wire drawing device controlled by the PLC controller can achieve precise force control and position control, ensure the repeatability and accuracy of each test, reduce human operation errors, and improve test efficiency;
2. Through the first visual detection component, the surface characteristics of the catheter are detected and analyzed in real time. During the test, the slight changes on the catheter surface can be observed and fed back immediately, and potential quality problems such as cracks and wear can be quickly identified, which improves the sensitivity of detection and instant feedback capabilities;
3. Through the cooperation of the first visual inspection component and the second visual inspection component, comprehensive geometric information of the bending part is provided. Through reverse measurement, key parameters such as the bending shape and curvature radius of the bending section can be accurately obtained, so as to optimize the product design according to the test results and ensure that the catheter meets the requirements of human anatomy;
4. The machine and components of the equipment are designed to be modular, which is convenient for rapid adjustment or replacement according to different test requirements, increasing the adaptability and scalability of the equipment, and suitable for testing catheters of various specifications;
5. The present invention combines physical tensile testing, surface quality inspection and three-dimensional morphological analysis, and can comprehensively evaluate the performance of the catheter from multiple dimensions, not only focusing on mechanical properties, but also considering the applicability and safety in practical applications;
6. Through integration with computer systems, test data is automatically collected and digitized, and detailed test reports are generated, which is convenient for quality control, research and analysis, and record management, and accelerates the decision-making process.

Figure: 1, machine; 1.1, installation notch; 2, catheter clamping assembly; 2.1, clamping unit; 3, first visual detection assembly; 3.1, first linear module; 3.2, first linear module; Two linear modules; 4, wire tension detection assembly; 4.1, tension unit; 4.11, clamping plane; 4.2, tension meter; 4.3, wire drawing assembly; 5, bending force detection assembly; 5.1, universal bracket; 5.2, metering dial; 5.3, force measuring probe; 6, second visual detection assembly; 7, PLC controller; 8, control panel; 9, display panel; 10, catheter; 10.1, straight section; 10.2, bending section; 11, bending force detection area; 12, tension detection area; 13, shading plate; 13.1, through port; 14, horizontal detection area.

DETAILED DESCRIPTION OF EMBODIMENTS

The technical scheme in the embodiment of the present invention will be clearly and completely described below in conjunction with the drawings in the embodiment of the present invention. Obviously, the described embodiment is only a part of the embodiment of the present invention, not all of the embodiments. Based on the embodiments in the present invention, all other embodiments obtained by ordinary technicians in this field without making creative work are within the scope of protection of the present invention.

It should be understood that although the terms upper, middle, lower, top, one end, etc. appear in this article to describe various elements, these elements are not limited by these terms. These terms are only used to distinguish elements from each other for easy understanding, and are not used to define any directional or sequential restrictions.

Figure 1:
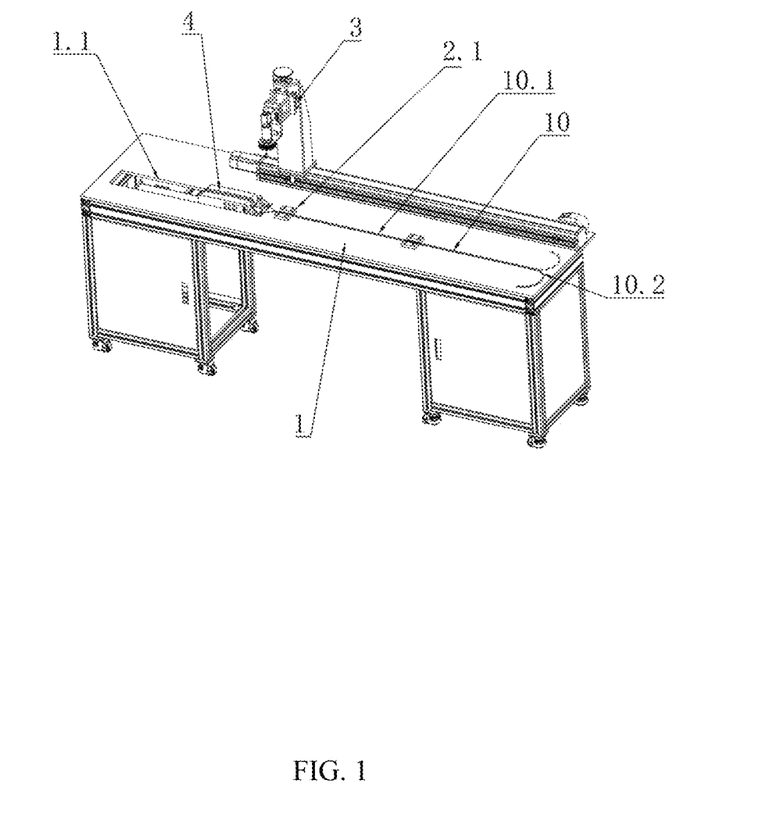
FIG. 1 is a schematic diagram of the overall structure of the present invention.
Figure 2:
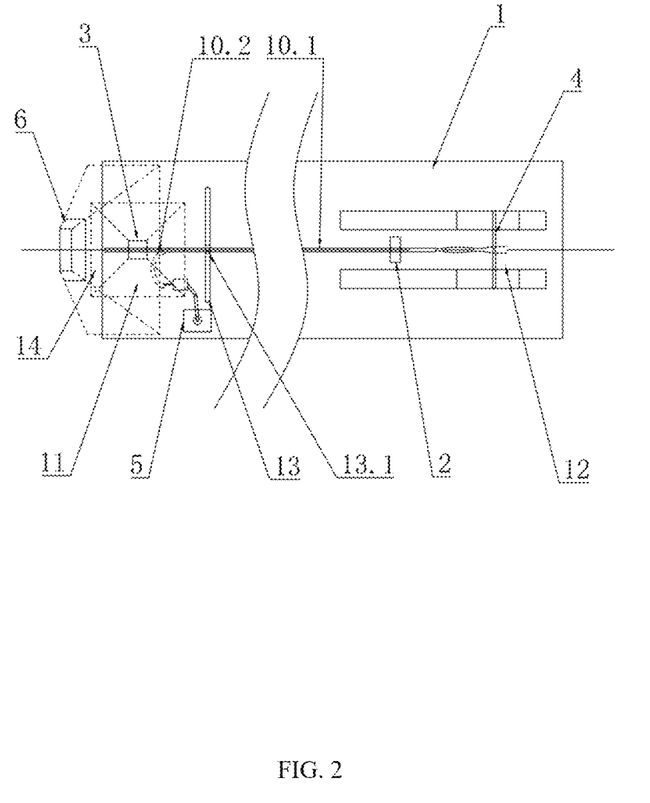
FIG. 2 is a schematic diagram of the layout of the present invention.
Figure 3:
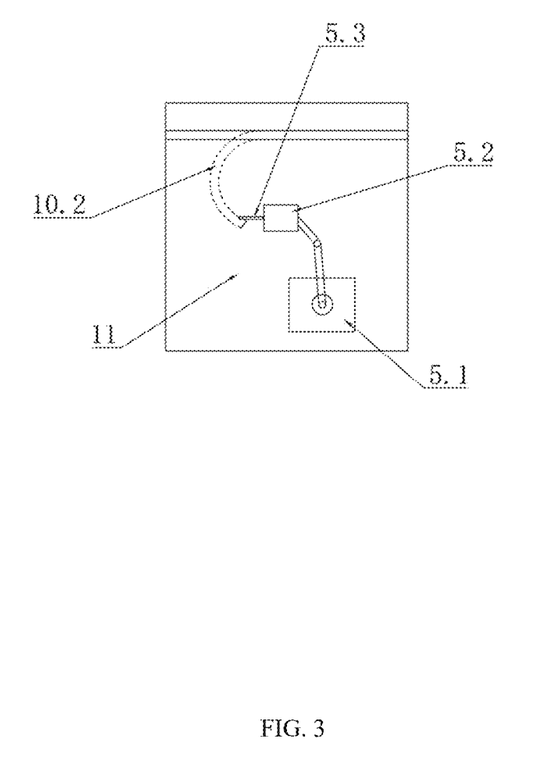
FIG. 3 is a schematic diagram of the bending force test area of the present invention.
Figure 4:
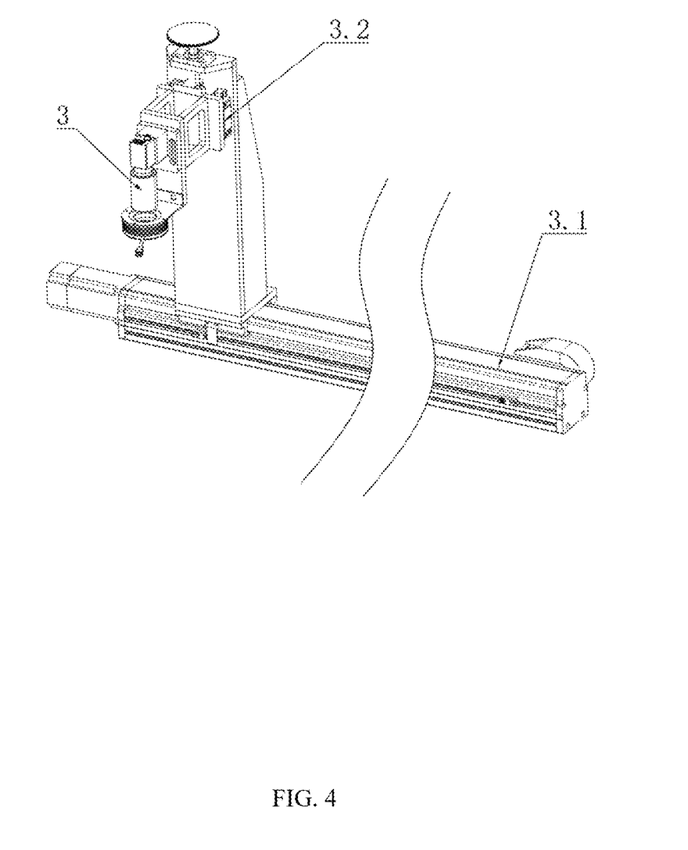
FIG. 4 is a schematic diagram of the structure of the first visual detection component of the present invention.
Figure 5:
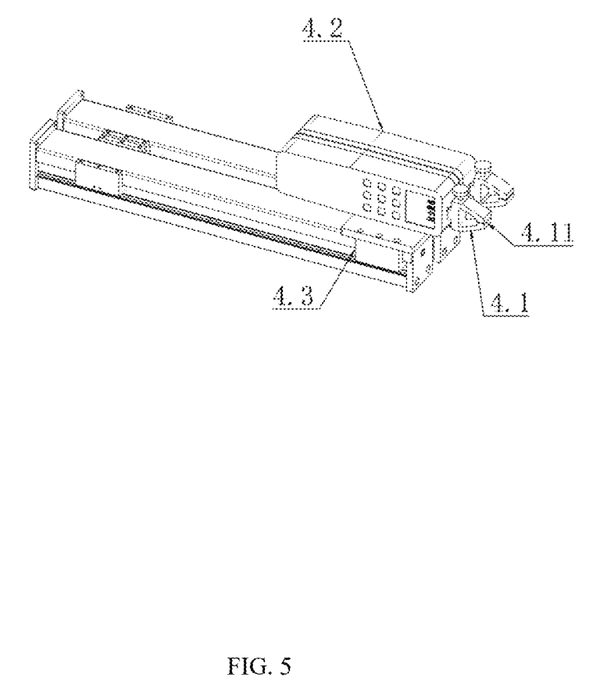
FIG. 5 is a schematic diagram of the structure of the wire tension detection component of the present invention.

As shown in FIGS. 1-7, a medical catheter testing device includes:

A machine 1, a catheter clamping assembly 2 linearly arranged on the machine 1, a first visual detection assembly 3 arranged parallel to one side of the catheter clamping assembly 2, a wire tension detection assembly 4 arranged at the operating end of the catheter 10, and a bending force detection assembly 5 arranged on one side of the bending section 10.2 of the catheter 10 and a second visual detection assembly 6 located at the end of the catheter 10. The machine 1 is also provided with a PLC controller 7 and a data acquisition and analysis module for receiving test results and providing control signals. The PLC controller 7 is connected to a control panel 8 and a display panel 9;

The catheter clamping assembly 2 includes a catheter clamping assembly 2 arranged along the catheter 10. At least two clamping units 2.1 are arranged in the axial direction of the straight section 10.1 of the tube 10 to position the tube 10 on the machine 1 in a linearly stretched posture;

The wire tension detection assembly 4 includes two tension units 4.1 arranged at the wire end of the tube 10, a tension meter 4.2 connected to the tension unit 4.1 in sequence, and a wire drawing assembly 4.3, wherein the action end of the wire drawing assembly 4.3 is connected to the tension unit 4.1 through the tension meter, wherein, as shown in FIG. 5, the wire drawing assembly 4.3 is a linearly moving module, which drives the bending section 10.2 of the tube 10 to bend by pulling and stretching the wire, and realizes the bending of the wire through the tension meter 4.2. Feedback the current tension value;

The first visual detection component 3 is arranged above the machine 1. The first visual detection component 3 is movable along the axis parallel to the catheter 10, and monitors and records the surface features of the catheter 10 and its bending section 10.2 during the test, so as to obtain the bending geometry information achieved by the bending section 10.2 with the set tension value or tension stroke, such as the bending radius and bending angle of the bending section 10.2;

The bending force detection component 5 is arranged on one side of the bending section 10.2 of the catheter 10, and docks with the bending section 10.2 after bending, so as to obtain the bending force of the bending section 10.2 under the current wire pulling stroke or tension value state;

The second visual detection component 6 is arranged along the axial direction of the catheter 10 and faces the end of the catheter 10. The second visual detection component 6 is used to monitor and feedback the horizontal position of the bending section 10.2 of the catheter 10, and the bending force detection component 5 is arranged facing the second visual detection component 6 to obtain the reading of the bending force of the bending section 10.2, and then obtain the bending force achieved by the bending section 10.2 with the set tension value or the wire pulling stroke;

The control panel 8 is arranged on the machine 1 and is electrically connected to the wire pulling force detection component 4. The control panel 8 controls and feedbacks the applied tension value and wire pulling stroke of the tension unit 4.1, and displays the current tension test data on the control panel 8;

The display panel 9 is electrically connected to the first visual detection component 3 and the second visual detection component 6, and obtains, displays and records the bending angle, bending radius and bending force under the current applied tension and actuation stroke parameters, as well as the current posture of the bending section 10.2. In the above embodiment, the second visual detection component 6 and the bending force detection component 5 define a bending force detection area 11 at the end of the catheter 10, the wire tension detection component 4 defines a tension detection area 12 at the front end of the catheter 10, and the first visual detection component 3 is arranged above the machine 1 and moves linearly between the tension detection area 12 and the bending force detection area 11 to detect the surface features of the catheter 10 and the posture and geometric information of the bending section 10.2 in real time during the current test phase. Through the above improvements, the entire test equipment is composed of modular components, and each area is clearly demarcated on the machine 1, which is convenient for rapid adjustment or replacement according to different test requirements, increasing the adaptability and expansibility of the equipment, and suitable for testing catheters 10 of various specifications.

Specifically, a shading plate 13 is provided near the boundary of the bending force detection area 11, and the shading plate 13 is specifically provided at the boundary of the bending force detection area 11, and can be adjusted along the axis of the straight section 10.1 of the catheter 10. For example, a plurality of bolt fixing positions are provided on the machine 1, and a through hole 13.1 for the catheter 10 to pass through is provided on the shading plate 13. The second visual detection component 6 is provided as a 3D scanning imaging system. By providing the shading plate 13, the influence of diffuse light is reduced, the diffuse reflected light is blocked, the light is made more concentrated and orderly, the interference of external light or stray light is effectively reduced, the accuracy and stability of observation are improved, and the imaging quality is improved.

As a further implementation of the clamping unit 2.1, the clamping unit 2.1 can be selected as a mechanical elbow clamp, and soft rubber or foam is provided on the clamping surface of the elbow clamp to reduce the damage to the surface of the catheter 10 caused by the clamping action. Of course, the clamping unit 2.1 can also be selected as a pneumatic elbow clamp, or an automatic clamping component controlled by electric control or oil pressure, the purpose of which is to improve the automation of the test work. As an example, a vertically acting clamping electric cylinder can be provided, and a clamping arm can be provided on the action end of the clamping cylinder to perform the clamping action.

As shown in FIGS. 1 and 4, as a further implementation of the pull wire tension detection component 4, in order to simulate the stretching state of the catheter 10 in the working environment, a mounting slot 1.1 is set on the machine 1, and the pull wire tension detection component 4 is placed in the mounting slot 1.1. The tension unit 4.1 extends from the mounting slot 1.1 to the surface of the machine 1, and the tension unit 4.1 has a clamping plane 4.11 for fixing the pull wire. By controlling the height of the pull wire tension detection component 4 in the mounting slot 1.1, the clamping plane 4.11 is flush with the axis of the straight section 10.1 of the catheter 10.

Among them, the number of tension units 4.1, tension gauge 4.2 and tension stretching components are all two, and they are all arranged in the same direction and parallel to the axis of the straight section 10.1 of the catheter 10, specifically, they are arranged on both sides of the axis of the straight section 10.1 of the catheter 10. The user can control the actuation stroke and tension value of the two tension units 4.1 through the control panel 8 and the PLC controller 7 respectively, and cycle the action of the tension unit 4.1, so as to simulate the working state of the catheter 10 under different conditions.

As can be seen from FIGS. 2 and 3, as a further improvement of the bending force detection component 5, the bending force detection component 5 includes a universal bracket 5.1, a metering dial 5.2 movably arranged on the universal bracket 5.1, and a force measuring probe 5.3 extending from the metering dial 5.2, wherein the universal bracket 5.1 is used to be fixed on the machine 1, and to adjust the relative positions of the metering dial 5.2 and the force measuring probe 5.3 in the bending force detection area 11, and the force measuring probe 5.3 is arranged on one side of the straight section 10.1 of the catheter 10 in the axial direction, and receives the bending section 10.2 of the catheter 10 after bending, so as to detect the bending force of the bending section 10.2 of the catheter 10.

As an example, the bending force detection component 5 can also be set as an electronically controlled force measuring meter, which is connected to the control panel 8 or the display panel 9 to feedback the current bending force value in real time and accurately.

As shown in FIG. 4, as a further explanation of the first visual detection component 3, the first visual detection component 3 includes an optical imager, a first linear module 3.1 for driving the optical imager to translate along the axis of the straight section 10.1 of the catheter 10, and a second linear module 3.2 arranged on the action end of the first linear module 3.1. The second linear module 3.2 is used to drive the optical imager to rise and fall vertically, thereby adjusting the focal length to obtain clear imaging, so as to improve the data accuracy of the bending angle and bending radius of the bending section 10.2, and display the above data on the real panel through the PLC controller 7 and the computer processing system.

As an implementation of the second visual detection component 6, the second visual detection component 6 is set as a 3D scanning imaging system. The second visual detection component 6 scans the current posture of the catheter 10 and establishes a three-dimensional model to obtain the geometric information of the bending section 10.2 of the catheter 10. The computer processing system and the 3D scanning imaging system are used to provide simulation and analyze and calculate the specific parameters of the bending state, so as to evaluate whether the performance of the catheter 10 meets the design requirements.

Figure 6:
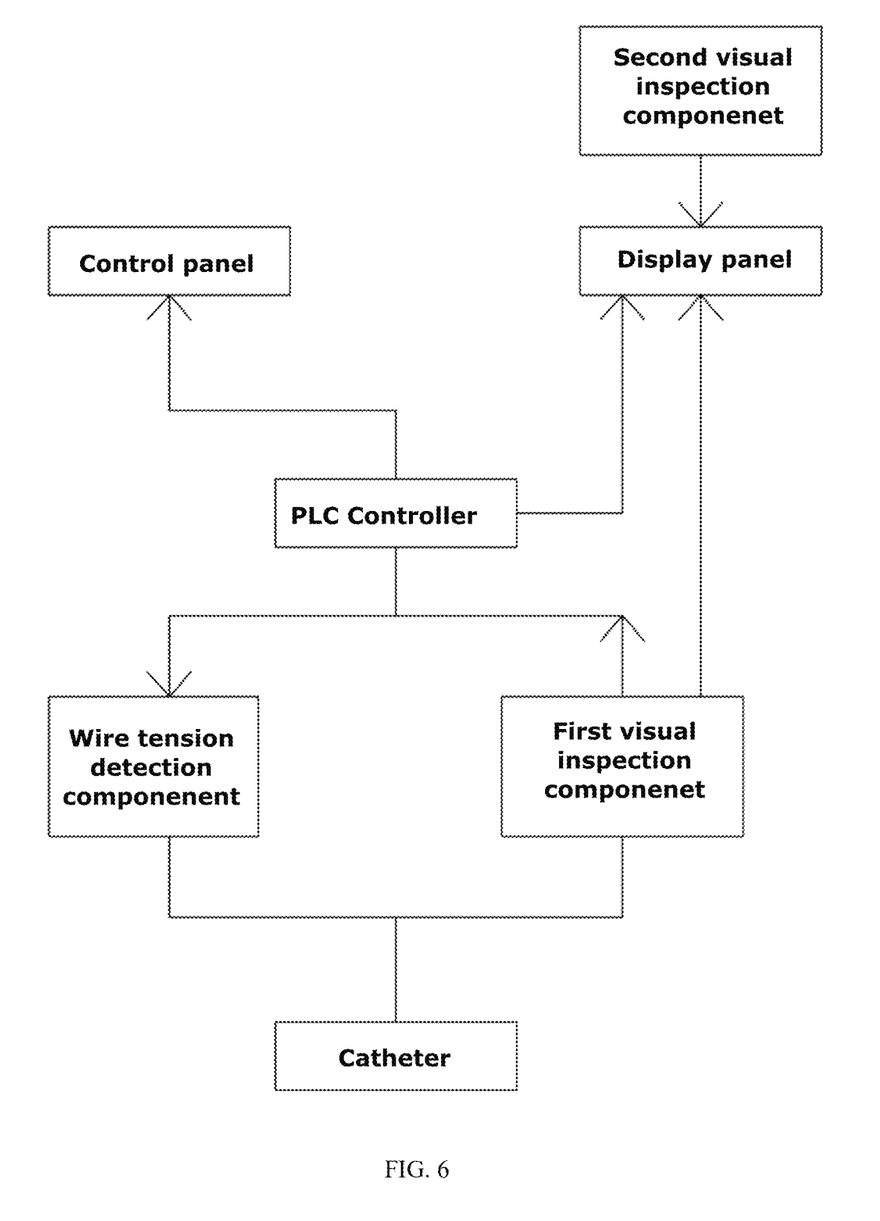
FIG. 6 is a connection block diagram of the present invention.

In the above embodiment, a computer processing system is also included, and the control panel 8, the display panel 9, and the PLC controller 7 are connected to the computer processing system to integrate the test data.

As a further improvement to the control panel 8, the control panel 8 also displays the tension test data of the tension unit 4.1 through the PLC controller 7. The tension test data includes the current actuation position, stretching speed, and stretching times of the wire in the current test phase, as well as the tension value set in the current test phase and the current real-time tension value. In addition, the PLC controller 7 can also control the movement and zeroing action of the wire drawing component 4.3;

The control panel 8 also displays the movement speed and current position of the first visual detection component 3 through the PLC controller 7.

Figure 7:
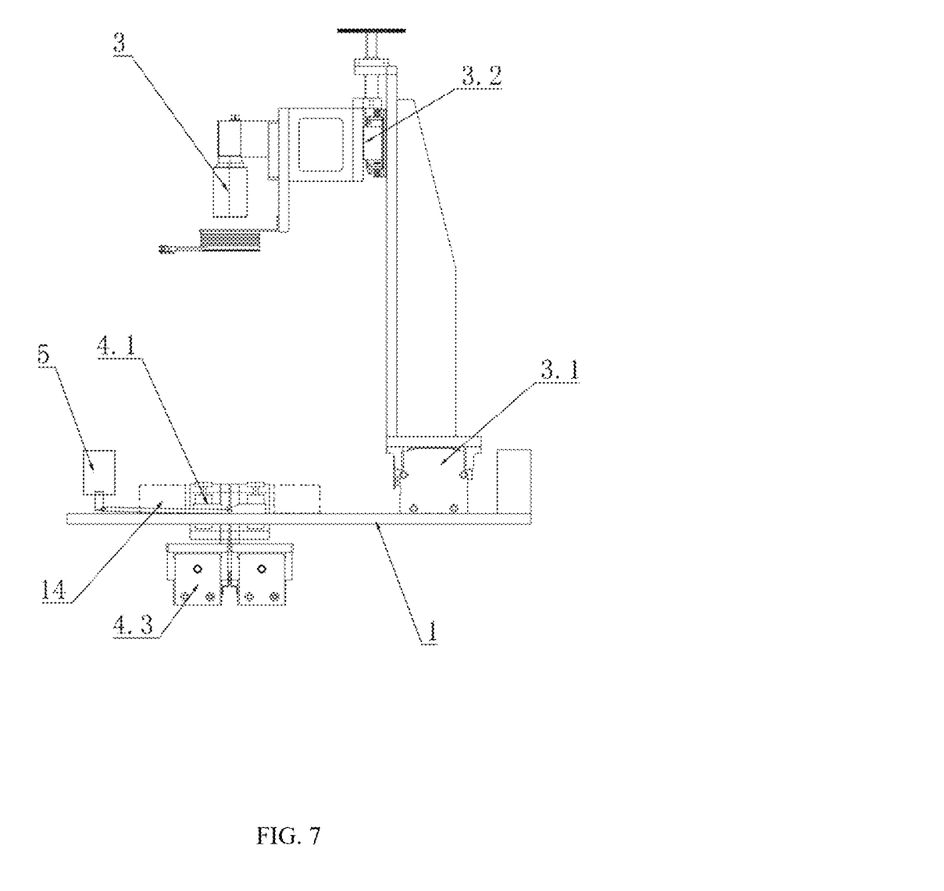
FIG. 7 is a schematic diagram of the horizontal detection area of the present invention.

As a further improvement to the display panel 9, the display panel 9 obtains the current posture of the catheter 10 through the first visual detection component 3, and obtains the current reading and posture of the bending force detection component 5 through the second visual detection component 6. The second visual detection component 6 obtains the reference position according to the axis of the straight section 10.1 of the catheter 10, and defines a horizontal detection area 14 on both sides of the reference position. The second visual detection component 6 obtains whether the position of the bending section 10.2 enters the horizontal detection area 14. If the bending section 10.2 enters the horizontal detection area 14, the horizontal angle of the bending section 10.2 is calculated.

The present invention also provides a testing method for a medical adjustable bend test device, comprising the following steps:

S1, mounting the catheter 10 on the machine 1, and fixing the catheter 10 through the clamping unit 2.1 after adjusting the horizontality of the catheter 10, connecting the bending wire with the tension unit 4.1;

S2, setting the tension test parameters and the tension stroke, and setting the number of cycles in the current test phase;

S3, the wire tension detection component 4 is activated, and the two tension units 4.1 reciprocate to pull the wire;

S4, the bending force detection component 5 tests the bending force, and the first visual detection component 3 collects the image of the bending section 10.2 of the catheter 10 after bending in place, and fits and records the bending radius and the bending angle, and records the tension value during the cyclic bending process;

S5, outputting a report.

In other embodiments, the PLC controller 7, the display panel 9 and the control panel 8 are also connected to a computer processing system, which includes at least a data acquisition and analysis module and performs the following steps:

In step S1, the test phase and quality control rule conditions are planned, and a storage database is constructed according to the test phase. The test phase refers to setting the expected working posture of the bending section 10.2 and testing the tension test data under the current posture, wherein the working posture can be defined by one or more of the bending angle, bending radius and bending force of the bending section 10.2;

Or setting the expected tension value, testing the working posture and wire position of the bending section 10.2;

Or setting the predetermined wire position, testing the working posture and tension value of the bending section 10.2;

After defining the test phase, setting the number of cycles and the cycle rule, the wire tension detection component 4 actuates the wire reciprocating motion, and tests the fatigue strength of the catheter 10.

In step S1, the pulling stroke or pulling force value of the pulling force unit 4.1 gradually increases with the number of actions during the test until the bending section 10.2 reaches the expected bending posture, so as to obtain the bending posture of the catheter 10 in each test parameter.

In step S2, the current horizontal position of the catheter 10 is retrieved. If the catheter 10 is within the predetermined horizontal detection area 14, the current horizontality data of the catheter 10 is retrieved and matched to the horizontal detection range. If the horizontality data does not meet the horizontal detection range, an error is reported on the control panel 8 or the display panel 9, and the PLC controller 7 controls the wire tension detection component 4 to return to its position; if the horizontality data is within the horizontal detection range, the PLC controller 7 drives the wire tension detection component 4 to perform the test phase action;

In steps S3 and S4, with the reciprocating movement of the first visual detection component 3, the test data and the surface features of the catheter 10, as well as the number of actions, are acquired and collected. The test data includes tension test data and geometric information of the bending section 10.2, as well as three-dimensional data of the bending posture of the bending section 10.2, and the items and values of the test data are mapped to the storage database for storage;

In step S5, in the current test phase, the test data is matched with the expected quality control rule conditions, and the data groups that pass the quality control and fail the quality control are marked respectively, and then the data report is output.

In step S1, the action rule of the wire tension detection component 4 is set, and the action is cyclical. At this time, the first visual detection component 3 reciprocates and monitors the surface features of the catheter 10. After adjusting the horizontal position of the catheter 10, the initial surface feature pattern of the catheter 10 is obtained and recorded, and the surface features of the catheter 10 are proofread in real time during the reciprocating movement of the first visual detection component 3. If there are bad fatigue features such as fractures and wear marks, take photos and record them, and store them in the storage database with the current tension test data and time node, and output them in the data report.

Further, after the first visual detection component 3 identifies the bad fatigue feature, it moves to the bad fatigue feature part of the catheter 10 through the first linear module 3.1, and the second linear module 3.2 drives the optical imager downward to obtain the enlarged image of the fatigue feature part, and stores it in the storage database with the current tension test data and time node, and outputs it in the data report.

In step S3, in the current test phase, the tension value and the current geometric information of the catheter 10 are recorded on the time axis, and the surface feature image of the catheter 10, the working posture and geometric information of the catheter 10 are matched with the time node, and output in the data report. In step S4, the computer processing system constructs a quality control self-check table through the data acquisition and analysis module. The quality control self-check table includes quality control rule condition items and self-check troubleshooting items, and the quality control pass or fail is mapped to the results of the quality control rule condition items, so as to facilitate quality control and research analysis, and provide improvement directions and traceability guidance for the modification design of the bending section 10.2 of the catheter 10.

In the above embodiment, the quality control rule condition refers to the geometric information expected to be achieved by the catheter 10 under the set test parameters, or the expected tension and tension stroke applied to the pull line of the catheter 10 under the set geometric information of the catheter 10. This specific embodiment is merely an explanation of the present invention and is not a limitation of the present invention. After reading this specification, those skilled in the art may make non-creative modifications to the present embodiment as needed. However, as long as they are within the scope of the claims of the present invention, they are protected by the patent law.

What is claimed is:

1. A medical catheter testing device, characterized in that it comprises: a machine platform (1), a catheter clamping assembly (2) linearly arranged on the machine platform (1), a first visual detection assembly (3) arranged in parallel on one side of the catheter clamping assembly (2), a wire tension detection assembly (4) arranged at a wire pulling end of a catheter (10), and a bending force detection assembly (5) arranged on one side of a bending section (10.2) of the catheter (10) and a second visual detection assembly (6) located at a second end of the catheter (10), wherein the machine platform is also provided with a PLC controller (7) and a data acquisition and analysis module for receiving test results and providing control signals, and the PLC controller (7) is connected to a control panel (8) and a display panel (9);

wherein the catheter clamping assembly (2) includes at least two clamping units (2.1) arranged along an axial direction of a straight section (10.1) of the catheter (10), and a clamping unit (2.1) positions the catheter (10) on the machine platform (1) in a linearly extended posture;

wherein the wire tension detection assembly (4) includes two tension units (4.1) arranged at the wire pulling end of the catheter (10), a tension meter (4.2) connected to a tension unit (4.1) in sequence, and a wire drawing assembly (4.3);

wherein the first visual detection assembly (3) is movably arranged in a direction parallel to the axis of the straight section (10.1) of the catheter (10), and monitors and records surface features of the catheter (10) under test conditions;

wherein the bending force detection assembly (5) is arranged on one side of the bending section (10.2) of the catheter (10), and docks with the bending section (10.2) after bending to obtain a bending force of the bending section (10.2) under a current wire pulling stroke or tension value;

wherein the second visual detection assembly (6) is axially arranged at an end facing the catheter (10), and monitors and feeds back the bending section (10.2), and the bending force detection assembly (5) is arranged facing the second visual detection assembly (6) to obtain a reading of the bending force of the bending section (10.2);

wherein the control panel (8) is electrically connected to the wire tension detection assembly (4), and controls and feeds back a current tension value and wire pulling stroke of the tension unit (4.1);

wherein the display panel (9) is electrically connected to the first visual detection assembly (3) and the second visual detection assembly (6), and obtains, displays and records a current tension value and a bending angle, bending radius and bending force under a wire pulling stroke state, as well as a current posture of the bending section (10.2);

wherein the bending force detection assembly (5) includes a universal bracket (5.1), a metering dial (5.2) movably arranged on the universal bracket (5.1) and a force measuring probe (5.3) extending from the metering dial (5.2), wherein the force measuring probe (5.3) is arranged on one side of a linear direction of the catheter (10), and receives the bending section (10.2) of a bent catheter (10) to detect a bending force of a bending section (10.2) of the catheter (10).

2. A medical catheter testing device according to claim 1, characterized in that: the second visual detection assembly (6) and the bending force detection assembly (5) define a bending force detection area (11) at an end of the catheter (10), the wire tension detection assembly (4) defines a tension detection area (12) at a front end of the catheter (10), and the first visual detection assembly (3) is arranged above the machine platform (1) and moves linearly between the tension detection area (12) and the bending force detection area (11).

3. A medical catheter testing device according to claim 2, characterized in that: the bending force detection area (11) is provided with a shading plate (13) close to a boundary of the bending force detection area (11), and the shading plate (13) is provided with a through hole (13.1) for the catheter (10) to pass through.

4. A medical catheter testing device according to claim 1, characterized in that: the machine platform (1) is provided with a mounting notch (1.1), the wire tension detection assembly (4) is placed in the mounting notch (1.1), a tension unit (4.1) extends out of the mounting notch (1.1), and the tension unit (4.1) that extends out of the mounting notch has a clamping plane (4.11) for fixing a pull wire, and the clamping plane (4.11) is flush with the axis of the straight section (10.1) of the catheter (10).

5. A medical catheter testing device according to claim 1, characterized in that: the control panel (8) also displays a current wire position, a number of stretches, a preset test tension, a real-time tension, and a stretching speed of a tension unit (4.1) in a current test phase through the PLC controller (7);

the control panel (8) also displays a moving speed and current position of the first visual detection assembly (3) through the PLC controller (7).

6. A medical catheter testing device according to claim 1, characterized in that: the display panel (9) obtains a current posture of the catheter (10) through the first visual detection assembly (3), and obtains a current reading and current posture of the bending force detection assembly (5) through the second visual detection assembly (6), and the second visual detection assembly (6) obtains a reference point according to the axis of the straight section (10.1) of the catheter (10), and defines a horizontal detection area (14) on both sides of the reference point, and the second visual detection assembly (6) obtains the bending section (10.2) in a horizontal detection area (14) to calculate the horizontal angle of the bending section (10.2).

7. A test method for the medical catheter test equipment according to claim 6, characterized in that it comprises the following steps:

S1, mounting the catheter (10) on the machine (1), and fixing the catheter (10) by the clamping unit (2.1) after adjusting horizontality of the catheter (10), and then connecting the bending wire to the tension unit (4.1);

S2, setting tension test parameters, and setting a number of cycles in the current test phase;

S3, activating the wire tension detection assembly (4), causing the two tension units (4.1) reciprocate to pull the wire;

S4, measuring the bending force with the bending force detection assembly (5) wherein the first visual detection assembly (3) collects an image of the bending section (10.2) of the catheter after bending in place, and fits and records the bending radius and bending angle, and records the tension value during the cyclic bending process;

S5, outputting a report.

8. A test method for a medical catheter test device according to claim 7, characterized in that: in step S4, the second visual detection assembly (6) is a 3D scanning imaging system, and the second visual detection assembly (6) obtains geometric information of the bending section (10.2) of the catheter (10) and establishes a three-dimensional model.

9. A test method for a medical catheter test device according to claim 8, characterized in that: the PLC controller (7), the display panel (9) and the control panel (8) are also connected to a computer processing system, and the following steps are performed:

in step S1, test phase and quality control rule conditions are planned, and a storage database is constructed according to one or more test phases;

wherein the one or more test phases refers to setting an expected working posture of the bending section (10.2), testing tension test data under a current posture, or setting an expected tension value, testing a working posture and wire position of the bending section (10.2), or setting a predetermined wire position and testing a working posture and tension value of the bending section (10.2);

in step S2, a current horizontal position of the catheter (10) is retrieved; if the catheter (10) is within a predetermined horizontal detection area (14), a current horizontality data of the catheter (10) is retrieved and matched to a horizontal detection range; wherein, if horizontality data does not meet the horizontal detection range, an error is reported on the control panel (8) or the display panel (9), and the PLC controller (7) controls the wire tension detection assembly (4) to return to its original position; and wherein, if the horizontality data is within the horizontal detection range, the PLC controller (7) drives the wire tension detection assembly (4) to move;

in steps S3 and S4, test data and data pertaining to surface features of the catheter (10), as well as a number of actions, are acquired and collected; wherein the test data includes tension test data and geometric information pertaining to the bending section (10.2), as well as three-dimensional data pertaining to the bending posture of the bending section (10.2), and values of the test data are mapped to the storage database;

in step S5, the test data is matched with expected quality control rule conditions, and test stage data groups that pass quality control and fail quality control are marked respectively, and then a data report is output.

* * * * *